US008110592B2

(12) United States Patent
Vermeer et al.

(10) Patent No.: US 8,110,592 B2
(45) Date of Patent: Feb. 7, 2012

(54) AGROCHEMICAL FORMULATIONS THAT CAN BE DISPERSED IN WATER CONTAINING POLYALKOXYTRIGLYCERIDES AS PENETRATION ENHANCES

(75) Inventors: Ronald Vermeer, Leverkusen (DE); Peter Baur, Schondorf (DE)

(73) Assignee: Bayer Cropscience AG, Monheim (DE)

( * ) Notice: Subject to any disclaimer, the term of this patent is extended or adjusted under 35 U.S.C. 154(b) by 79 days.

(21) Appl. No.: 12/442,496

(22) PCT Filed: Sep. 18, 2007

(86) PCT No.: PCT/EP2007/008099
§ 371 (c)(1),
(2), (4) Date: Mar. 23, 2009

(87) PCT Pub. No.: WO2008/037377
PCT Pub. Date: Apr. 3, 2008

(65) Prior Publication Data
US 2009/0247597 A1   Oct. 1, 2009

(30) Foreign Application Priority Data
Sep. 30, 2006   (EP) .................................. 06020676

(51) Int. Cl.
*A01N 43/64*   (2006.01)
*A01P 3/00*   (2006.01)
(52) U.S. Cl. ...................... 514/383; 546/282.1; 504/348; 504/365; 504/116.1; 514/378; 424/405
(58) Field of Classification Search .................... None
See application file for complete search history.

(56) References Cited

U.S. PATENT DOCUMENTS

| 4,443,971 | A |   | 4/1984  | Chaleff              |         |
|-----------|---|---|---------|----------------------|---------|
| 4,761,373 | A |   | 8/1988  | Anderson et al.      |         |
| 5,013,659 | A |   | 5/1991  | Bedbrook et al.      |         |
| 5,162,602 | A |   | 11/1992 | Somers et al.        |         |
| 5,254,799 | A |   | 10/1993 | De Greve et al.      |         |
| 5,290,751 | A |   | 3/1994  | Fiard et al.         |         |
| 5,378,824 | A |   | 1/1995  | Bedbrook et al.      |         |
| 5,428,147 | A |   | 6/1995  | Barker et al.        |         |
| 5,498,830 | A |   | 3/1996  | Barry et al.         |         |
| 5,824,798 | A |   | 10/1998 | Tallberg et al.      |         |
| 6,147,278 | A |   | 11/2000 | Rogers et al.        |         |
| 6,215,042 | B1 |   | 4/2001  | Willmitzer et al.    |         |
| 6,403,529 | B1 | * | 6/2002  | Wollenweber et al.   | 504/363 |
| 6,596,873 | B1 | * | 7/2003  | Lieb et al.          | 546/256 |
| 2002/0155954 | A1 | * | 10/2002 | Aven              | 504/348 |
| 2003/0097686 | A1 |   | 5/2003  | Knauf et al.      |         |
| 2003/0144148 | A1 |   | 7/2003  | Milius et al.     |         |
| 2004/0157745 | A1 |   | 8/2004  | Vermeer et al.    |         |
| 2005/0032647 | A1 |   | 2/2005  | Deckwer et al.    |         |
| 2007/0053944 | A1 |   | 3/2007  | Vermeer            |         |
| 2007/0281860 | A1 | * | 12/2007 | Baur et al.       | 504/223 |
| 2008/0153706 | A1 |   | 6/2008  | Frisch et al.     |         |

FOREIGN PATENT DOCUMENTS

| EP | 0490781      |   | 6/1992  |
|----|--------------|---|---------|
| EP | 0131624 B1   |   | 9/1992  |
| WO | WO 98/09516  |   | 3/1993  |
| WO | WO 98/18321  |   | 5/1995  |
| WO | WO 99/60851  |   | 12/1999 |
| WO | WO 00/01233  |   | 1/2000  |
| WO | WO 03/000053 |   | 1/2003  |
| WO | WO 2004/054364 |   | 7/2004 |
| WO | WO 2005/084435 | * | 9/2005 |
| WO | WO 2005/084437 | * | 9/2005 |
| WO | WO 2006/114186 |   | 11/2006 |
| WO | WO 2007/003319 |   | 1/2007 |

OTHER PUBLICATIONS

Chemistry World 4(11), 2007 (www.rsc.org/chemistryworld/Issues/2007/November/NewInsecticidesGetReadyForMarket.asp).*
Haefs et al. in Pesticide management Science 58:825-833 (2002).*
Downey, R.K. in 1990. Canola: A quality brassica oilseed. p. 211-217. In: J. Janick and J.E. Simon (eds.), Advances in new crops. Timber Press, Portland, OR.*
Cotterill J.V. et al.: "Improving the persistence of a formulation of the avian repellent cinnamamide, for the protection of autumn-sown oilseed rape" Pest Management Science vol. 60, No. 10, Oct. 2004, pp. 1019-1024, XP002432280 ISSN: 1526-498X; p. 1020, left hand column, p. 1021, paragraph 2.4.4; p. 1023-pf 1024.
Haefs R. et al: "Studies on a new group of biodegradable surfactants for glyphosate" Pest Management Science, vol. 58, No. 8, Aug. 2002, p. 825-833 XP002432281 ISSN: 1526-498X cited in he application p. 826 left hand column, p. 827 right hand column, p. 829 right hand column-p. 832.
Romano-Gotshc, R International Search Report WIPO PCT/EP2007/008099; Sep. 11, 2008, pp. 1-10.
Cotterill, Jane V., "Improving the Persistence of a Formulation of the Avian Repellent Cinnamamide, for the Protection of Autumn-Sown Oilseed Rape," Pest Management Science, vol. 60, No. 10, Oct. 2004, Doc. XP-002432280. pp. 1019-1024.
Haefs, Roland, "Studies on a New Group of Biodegradable Surfactants for Glyphosate," Pest Management Science, vol. 58, No. 8, Aug. 2002, Doc. XP-002432281, pp. 825-833.
Braun, Hans-Peter et al., "The General Mitochondrial Processing Peptidase from Potato is an Integral Part of Cytochrome C Reductase of the Respiratory Chain," The EMBO Journal, vol. 11, No. 9, 1992, Oxford University Press, pp. 3219-3227.
Christou, Paul, "Transformation Technology," Trends in Plant Science, vol. 1, No. 12, Dec. 1996, Elsevier Science Ltd., pp. 423-431.
Haefs, Roland et al., "Studies on a New Group of Biodegradable Surfactants for Glyphosate," Pest Management Science, No. 58, 2002, Society of Chemical Industry, pp. 825-833.
Wolter, Frank P. et al., "rbcS Genes in *Solanum tuberosum*: Conservation of Transit Peptide and Exon Shuffling During Evolution," Proc. Natl. Acad. Sci. USA, vol. 85, Feb. 1988, pp. 846-850.

(Continued)

Primary Examiner — Brandon Fetterolf
Assistant Examiner — Dennis Heyer
(74) Attorney, Agent, or Firm — Baker Donelson Bearman, Caldwell & Berkowitz, PC

(57) ABSTRACT

The present invention relates to novel water-dispersible agrochemical formulations such as, for example, water-based suspension concentrates and water-dispersible granules of agrochemically active compounds comprising a penetrant from the class of the polyalkoxytriglycerides, to a process for preparing these formulations and to their use for applying the active compounds comprised therein.

7 Claims, No Drawings

OTHER PUBLICATIONS

Sonnewald, Uwe et al., "Transgenic Tobacco Plants Expressing Yeast-Derived Invertase in Either the Cytosol, Vacuole or Apoplast: A Powerful Tool for Studying Sucrose Metabolism and Sink/Source Interactions," The Plant Journal, No. 1, 1991, pp. 95-106.

* cited by examiner

AGROCHEMICAL FORMULATIONS THAT CAN BE DISPERSED IN WATER CONTAINING POLYALKOXYTRIGLYCERIDES AS PENETRATION ENHANCES

CROSS REFERENCE TO RELATED APPLICATIONS

This application is a §371 National Stage Application of PCT/EP2007/008099 Sep. 18, 2007 which claims priority to European Application 06020676.0 filed Sep. 30, 2006.

BACKGROUND OF THE INVENTION

1. Field of the Invention

The present invention relates to novel water-dispersible agrochemical formulations such as, for example, water-based suspension concentrates and water-dispersible granules of agrochemically active compounds, to a process for preparing these formulations and to their use for applying the active compounds comprised therein.

2. Description of Related Art

To unfold their biological action, systemic agrochemically active compounds, in particular systemic insecticides and fungicides, require a formulation which allows the active compounds to be taken up by the plant/the target organisms. Accordingly, systemic agrochemically active compounds are usually formulated as an emulsion concentrate (EC), as a soluble liquid (SL) and/or as an oil-based suspension concentrate (OD). In an EC formulation and in an SL formulation, the active compound is present in dissolved form; in an OD formulation, the active compound is present as a solid. In general, a suspension concentrate (SC) or water-dispersible granules (WG) are technically also feasible. Hereinbelow, only suspension concentrates are described; however, this is meant to include other types of formulation where the active compound is present in a water-dispersible form. However, to achieve a satisfactory biological action when using SC formulations, it is necessary for the active compound in the SC to be combined with an additive. In this context, an additive is a component which improves the biological action of the active compound, without the component for its part having a biological action. In particular, an additive permits/facilitates the uptake of the active compound into the leaf (penetrant). A penetrant may be incorporated into the formulation of the agrochemically active compound (in-can formulation) or be added after dilution of the concentrated formulation of the spray liquor (tank-mix). To avoid dosage errors and to improve user safety during application of agrochemical products, it is advantageous to incorporate the penetrants into the formulation. This also avoids the unnecessary use of additional packaging material for the tank-mix products.

Some water-based suspension concentrates of agrochemically active compounds comprising penetrants are already known. Thus, WO 05/036963 describes formulations of this type which, in addition to certain fungicides, also comprise at least one penetrant from the group of the alkanolethoxylates. WO 99/060851 describes various alkanolethoxylates based on fatty alcohols.

A disadvantage of the formulations, mentioned above, with penetrants is the fact that, in particular in the case of application to leaves, fruits or other parts of plants in sensitive crop plants, such as pome fruit (for example *Malus domestica*, *Pyrus communis*), stone fruit (*Prunus armeniaca*, *Prunus domestica*, *Prunus persica*), citrus crops, vegetables, such as, for example, bell peppers (*Capsicum annuum*) and cantaloupes (*Cucumis melo*), and also ornamental plants, such as roses, the spray liquor residue left after application and drying of the spray liquid may cause damage to the plants.

Furthermore, Pest. Manag. Sci. 58:825-833 (2002) discloses triglyceride ethoxylates (Agnique® RSO series) which are recommended for use as tank-mix penetrants for systemic water-soluble agrochemically active compounds. As an advantage of these auxiliaries, the plant compatibility on weeds was mentioned. This is characterized by having no effect on photosynthesis, which is advantageous for the systemic action of phloem-mobile active compounds such as glyphosate. However, the spray liquor concentrations required for a satisfactory uptake of active compound were between 1 and 10 g/l, which is incompatible with an in-can formulation.

US 2002/01 55954 mentions triglyceride ethoxylates which reduce the surface tension of the spray liquor to less than 40 mN/m as additives. In this application, the triglyceride ethoxylates are described in an in-can formulation. However, because of their origin, the castor oil-based triglyceride ethoxylates described in this publication differ significantly, structurally, from the triglyceride ethoxylates according to the invention. Castor oil is a vegetable oil which has a hydroxy functionality in the aliphatic side chains, therefore requiring an additional ethoxylation in this position. This is in contrast to the triglyceride ethoxylates according to the invention which are ethoxylated only between the glyceride unit and the various aliphatic side chains.

SUMMARY OF THE INVENTION

It is an object of the present invention to develop stable, storable, water-based suspension concentrates comprising at least one penetrant, without adversely affecting plant compatibility.

It has been found that this object is achieved by water-dispersible agrochemical formulations comprising a penetrant from the class of the polyalkoxytriglycerides. Accordingly, the present invention provides water-dispersible agrochemical formulations, comprising
  at least one agrochemically active compound which is solid at room temperature,
  at least one penetrant from the class of the polyalkoxytriglycerides.

DETAILED DESCRIPTION OF A PREFERRED EMBODIMENT

The compositions according to the invention are preferably liquid suspension concentrates comprising
  at least one agrochemically active compound which is solid at room temperature,
  at least one penetrant from the class of the polyalkoxytriglycerides, where the triglyceride is of vegetable origin,
  at least one nonionic surfactant and/or at least one anionic surfactant and
  optionally one or more additives from the groups of the antifreeze agents, the antifoams, the preservatives, the antioxidants, the spreading agents, the colorants and/or the thickeners.

Preference is also given to water-dispersible granules which can be prepared by customary methods, comprising
  at least one agrochemically active compound which is solid at room temperature,
  at least one penetrant from the class of the polyalkoxytriglycerides, where the triglyceride is of vegetable origin, optionally further formulation auxiliaries from the groups of the emulsifiers, the nonionic and/or anionic surfactants, the antifoams, the preservatives, the antioxidants, the colorants and/or the inert fillers.

Furthermore, it has been found that water-based suspension concentrates according to the invention can be prepared by mixing together at least one agrochemically active compound which is solid at room temperature, at least one penetrant from the class of the polyalkoxytriglycerides, where the triglyceride is of vegetable origin, at least one nonionic surfactant and/or at least one anionic surfactant and optionally one or more additives from the groups of the antifreeze agents, the antifoams, the preservatives, the antioxidants, the spreading agents, the colorants and/or a thickener and optionally subsequently grinding the suspension formed.

Finally, it has been found that the suspension concentrates according to the invention are highly suitable for applying the agrochemically active compounds comprised therein to plants and/or their habitat.

The formation of plant damage is complex and can be traced back to the penetration of penetrants such as alkanolethoxylates in particular at the edge of the spray droplets on the plant. This may result in high local concentrations of additive and/or active compound, causing necrotic rings or circles to appear on the treated plant surface, the area of some of which will extend owing to the destruction of tissue. Surprisingly, it has now been found that the occurrence of necroses is associated with the presence of stomata or structures derived therefrom, such as, for example, lenticels. Furthermore, polyalkoxytriglycerides were found which facilitate the uptake of active compound but which, surprisingly and in contrast to other penetrants typically employed, do not lead to necroses. Thus, for example, the use of alkanolethoxylates—with or without active compound—on the underside of rose leaves at concentrations of 0.1-1 g/l results in strong ring necroses, whereas with polyalkoxytriglycerides—likewise with or without active compound—no necroses are observed. It is not known why necroses occur just with sensitive plants on the side of the leaf with stomata. Furthermore, it has been found that, at use concentrations of 0.1-1 g/l, these compatible polyalkoxytriglycerides are distinguished in that their spray liquors have surface tension values of more than 41 mN/m, in contrast to US 2002/0155954.

It is furthermore surprising that polyalkoxytriglycerides, such as, for example, rapeseed oil ethoxylate Crovol® CR70G (Croda) facilitates the uptake of very different substances (for example substances of differing lipophilicity, electrolytes and non-electrolytes), such as, for example, sulphonylureas, ketoenols, azol fungicides, etc. Here, in the case of the polyalkoxytriglycerides according to the invention, the uptake kinetics are distinguished in that, in contrast to known penetrants, penetration of the active compound takes place not preferably immediately after application, with a considerable decrease thereafter, but with very constant kinetics over a period of several days. This effect, too, affects plant compatibility positively since it is thus possible to avoid temporary high local concentrations of critically active compounds in the leaf tissue.

The incompatibility of herbicides is also crucially dependent on the rapid formation of high local concentrations in the treated organs of the crop plant. As a result, herbicides, such as, for example sulphonylureas, are less well tolerated in cereals when penetrants are used, which cause a rapid uptake of active compound after application. In contrast, a slow uptake of the herbicide is often tolerated well. Since the properties found of the polyalkoxytriglycerides, which for their part do not cause necroses and which facilitate the slow but long-lasting uptake of active compound from the spray coating also applies to herbicidally active compounds, there is a positive effect on the selectivity of herbicides compared to alkanolethoxylates or rapeseed oil methyl ester penetrants, for example.

Finally, it is extremely surprising that the suspension concentrates according to the invention have very good stability. The polyalkoxytriglycerides used, like the dispersants of a water-based suspension concentrate, have surfactant properties, which normally results in a competition with the dispersants. Especially at high storage temperature or after storage at changing temperature conditions, this results in a destabilization of the suspension concentrate.

Preferred embodiments of the subject of the invention are described below.

Suitable penetrants in the present context are polyalkoxytriglycerides. Polyalkoxytriglycerides can be prepared by alkoxylation of triglycerides. The alkoxylation of triglycerides gives substance mixtures in which one to three of the side chains are alkoxylated. In alkoxylations, a distinction may be made between ethoxylation, propoxylation, butoxylation or a mixture of these processes. For each of the side chains, the length of the unmodified side chains can vary from 9 to 24, preferably from 12 to 22, very preferably from 14 to 20, carbon atoms independently of the other side chains in the same molecule. These aliphatic side chains can be straight-chain or branched.

In a preferred embodiment of the present invention, the polyalkoxytriglycerides are obtained by ethoxylation of triglycerides.

In a particularly preferred embodiment of the present invention, the polyalkoxytriglycerides are obtained by ethoxylation of rapeseed oil, maize oil, palm kernel oil or almond oil.

In a very particularly preferred embodiment of the present invention, the polyalkoxytriglycerides are obtained by ethoxylation of rapeseed oil, the degree of ethoxylation being from 60 to 80% by weight.

Corresponding polyalkoxytriglycerides are known or can be prepared by known methods (commercially available, for example, under the names Crovol® A 70 UK, Crovol® CR 70 G, Crovol® M 70 and Crovol® PK 70 from Croda).

Suitable active compounds for use in the formulations according to the invention are all agrochemically active compounds which are solid at room temperature.

Preference is given to systemic fungicides, insecticides and herbicides.

Particular preference is given to active compounds from the classes of the azole fungicides (azaconazole, bitertanol, bromuconazole, cyproconazole, diclobutrazole, difenoconazole, diniconazole, diniconazole-M, epoxiconazole, etaconazole, fenarimol, fenbuconazole, fluquinconazole, flurprimidol, flusilazole, flutriafol, furconazole, furconazole-cis, hexaconazole, imazalil, imazalil sulphate, imibenconazole, ipconazole, metconazole, myclobutanil, nuarimol, oxpoconazole, paclobutrazole, penconazole, pefurazoate, prochloraz, propiconazole, prothioconazole, pyrifenox, simeconazole, tebuconazole, tetraconazole, triadimefon, triadimenol, triflumizole, triforin, triticonazole, uniconazole, voriconazole, viniconazole), strobilurin fungicides (azoxystrobin, dimoxystrobin, fluoxastrobin, kresoxim-methyl, metominostrobin, orysastrobin, picoxystrobin, pyraclostrobin, trifloxystrobin), the SDH fungicides, the chloronicotinyl insecticides (clothianidin, dinotefuran, imidacloprid, thiamethoxam, nitenpyram, nithiazin, acetamiprid, imidacloprid, nitenpyram, thiacloprid), the insecticidal ketoenols (spirodiclofen, spiromesifen, spirotetramate), fiproles (fiprole, ethiprole) and butenolides, and also pymetrozine, fluopicolid, N-(3',4'-dichloro-5-fluoro-1,1'-biphenyl-2-yl)-3-(difluoromethyl)-1-methyl-1H-pyrazole-4-carboxamide and N-{2-[3-chloro-5-(trifluoromethyl)-2-pyridinyl]ethyl}-2-(trifluoromethyl)benzamide. Particular preference is also given to herbicides, in particular sulfonylureas, triketones and herbicidal ketoenols, and also safeners.

Very particularly preferred as active compounds are the fungicides
tebuconazole,
prothioconazole,
N-(3',4'-dichloro-5-fluoro-1,1'-biphenyl-2-yl)-3-(difluoromethyl)-1-methyl-1H-pyrazole-4-carboxamide (known from WO 03/070705) of the formula

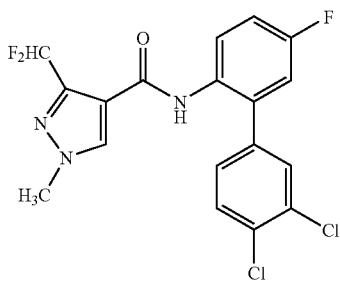

N-{2-[3-chloro-5-(trifluoromethyl)-2-pyridinyl]ethyl}-2-(trifluoromethyl)benzamide (known from WO 04/16088)
trifloxystrobin,
fluopicolid
the insecticides
imidacloprid,
thiamethoxam,
clothianidin,
thiacloprid,
spirotetramate,
fipronil,
ethiprol and
the herbicides
thiencarbazone
sulcotrione,
mesotrione,
tembotrione,
pyrasulfotole,
iodosulphuron,
mesosulphuron and
foramsulphuron.

Suitable nonionic surfactants are all compounds of this type which can usually be employed in agrochemical compositions. Polyethylene oxide/polypropylene oxide block copolymers, polyethylene glycol ethers of straight-chain alcohols, reaction products of fatty acids with ethylene oxide and/or propylene oxide, furthermore polyvinyl alcohol, polyvinylpyrrolidone, mixed polymers of polyvinyl alcohol and polyvinylpyrrolidone, mixed polymers of polyvinyl acetate and polyvinylpyrrolidone and also copolymers of (meth)acrylic acid and (meth)acrylic esters, furthermore alkyl ethoxylates and alkylaryl ethoxylates which may optionally be phosphated and may optionally be neutralized with bases, polyoxyamine derivatives and nonylphenol ethoxylates may be mentioned as being preferred.

Suitable anionic surfactants are all substances of this type which can usually be employed in agrochemical compositions. Preference is given to alkali metal and alkaline earth metal salts of alkylsulphonic acids or alkylarylsulphonic acids.

A further preferred group of anionic surfactants or dispersants are salts of polystyrenesulphonic acids, salts of polyvinylsulphonic acids, salts of naphthalenesulphonic acid/formaldehyde condensates, salts of condensates of naphthalenesulphonic acid, phenolsulphonic acid and formaldehyde and also salts of lignosulphonic acid.

Suitable antifoams are all substances which can usually be employed for this purpose in agrochemical compositions. Preference is given to silicone oils and magnesium stearate.

Suitable antioxidants are all substances which can usually be employed for this purpose in agrochemical compositions. Preference is given to butylated hydroxytoluene (2,6-di-t-butyl-4-methylphenol, BHT).

Suitable colorants are all substances which can usually be employed for this purpose in agrochemical compositions. Examples which may be mentioned are titanium dioxide, carbon black, zinc oxide and blue pigments and also permanent red FGR.

Suitable preservatives are all substances of this type which can usually be employed for this purpose in agrochemical compositions. Examples which may be mentioned are Preventol® (from Bayer AG) and Proxel®.

Suitable spreading agents are all substances which can usually be employed for this purpose in agrochemical compositions. Preference is given to polyether- or organo-modified polysiloxanes.

Suitable inert fillers are all substances which can usually be employed for this purpose in agrochemical compositions. Preference is given to inorganic particles, such as carbonates, silicates and oxides, and also organic substances, such as urea/formaldehyde condensates. Examples which may be mentioned are kaolin, rutile, silicon dioxide, what is known as highly disperse silica, silica gels, and also natural and synthetic silicates, furthermore talc.

Suitable emulsifiers are all customary nonionic, anionic, cationic and zwitterionic substances having surfactant properties which are usually employed in agrochemical compositions. These substances include reaction products of fatty acids, fatty esters, fatty alcohols, fatty amines, alkylphenols or alkylarylphenols with ethylene oxide and/or propylene oxide and/or butylene oxide, and also their sulphuric acid esters, phosphoric acid monoesters und phosphoric acid diesters, furthermore reaction products of ethylene oxide with propylene oxide, furthermore alkylsulphonates, alkyl sulphates, aryl sulphates, tetraalkylammonium halides, trialkylarylammonium halides and alkylaminesulphonates. The emulsifiers can be employed on their own or else as a mixture. Reaction products of castor oil with ethylene oxide in a molar ratio of from 1:20 to 1:60, reaction products of $C_6$-$C_{20}$-alcohols with ethylene oxide in a molar ratio of from 1:5 to 1:50, reaction products of fatty amines with ethylene oxide in a molar ratio of from 1:2 to 1:25, reaction products of 1 mol of phenol with from 2 to 3 mol of styrene and from 10 to 50 mol ethylene oxide, reaction products of $C_8$-$C_{12}$-alkylphenols with ethylene oxide in a molar ratio of from 1:5 to 1:30, alkylglycosides, $C_8$-$C_{16}$-alkylbenzenesulfonic acid salts, such as, for example, calcium, monoethanolammonium, diethanolammonium and triethanolammonium salts may be mentioned as being preferred.

Further emulsifiers are ethoxylated nonylphenols, reaction products of alkylphenols with ethylene oxide and/or propylene oxide, ethoxylated arylalkylphenols, furthermore ethoxylated and propoxylated arylalkylphenols, and also sulphated or phosphated arylalkylethoxylates or -ethoxypropoxylates, for example sorbitan derivatives, such as polyethylene oxide sorbitan fatty esters and sorbitan fatty esters.

Suitable antifreeze agents are all substances of this type which can usually be employed in agrochemical compositions. Preference is given to urea, glycerol and propylene glycol.

Suitable thickeners are all substances of this type which can usually be employed in agrochemical compositions. Preference is given to silicates (such as, for example, Attagel® 50 from Engelhard) or xanthan gum (such as, for example, Kelzan® S from Kelko).

The compositions according to the invention comprise in general from 1 to 60% by weight of one or more of the agrochemically active compounds which may be used according to the invention, preferably from 5 to 50% by weight and particularly preferably 10 to 30% by weight.

in general from 1 to 50% by weight of at least one penetrant according to the invention, preferably from 2 to 30% by weight and particularly preferably from 5 to 20% by weight.

in general from 1 to 20% by weight of at least one nonionic and/or at least one anionic surfactant, preferably from 2.5 to 10% by weight.

in general from 0.1 to 25% by weight of additives from the groups of the antifoams, the preservatives, the antioxidants, the spreading agents, the colorants and/or the thickeners, preferably from 0.1 to 20% by weight.

Compositions according to the invention in the form of water-dispersible granules generally comprise from 1 to 20% by weight of at least one penetrant according to the invention, preferably from 5 to 20% by weight.

The suspension concentrates according to the invention are prepared by mixing the particular desired ratios of the components with one another. The components may be mixed with one another in any order. Expediently, the solid components are employed in a finely ground state. However, it is also possible to subject the suspension formed after mixing of the components initially to a coarse grinding then to a fine grinding, so that the mean particle size is below 20 μm. Preferred are suspension concentrates in which the solid particles have a mean particle size of from 1 to 10 μm.

When carrying out the process according to the invention, the temperatures may be varied within a certain range. In general, the process is carried out at temperatures between 10° C. and 60° C., preferably between 15° C. and 40° C.

Suitable for carrying out the process according to the invention are customary mixers and grinders employed for producing agrochemical formulations.

The compositions according to the invention are formulations which remain stable even after prolonged storage at elevated temperatures or in the cold, since no crystal growth is observed. By dilution with water, they can be converted into homogeneous spray liquors.

The application rate of the compositions according to the invention can be varied within a relatively wide range. It depends on the agrochemically active compounds in question and their content in the compositions.

The compositions of the invention, which comprise at least one of the insecticidally active compounds of the invention, in combination with good plant tolerance, favourable toxicity to warm-blooded animals and high compatibility with the environment, are suitable for protecting plants and plant organs, for increasing the harvest yields, for improving the quality of the harvested material and for controlling animal pests, in particular insects, arachnids, helminths, nematodes and molluses, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophoruis* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is further possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii. Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Pvlacrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthczia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., Trialeurodes vaporariorum, *Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Fvhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Fleterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compositions according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms).

The compositions of the invention can in addition to the abovementioned agrochemically active compounds comprise other active compounds as mixing partners, such as insecticides, attractants, sterilants, bactericides, acaricides, nematicides, fungicides, growth-regulating substances, herbicides, safeners, fertilizers or semiochemicals.

Particularly favourable mixing partners are, for example, the following components:

Fungicides:
Inhibitors of Nucleic Acid Synthesis
benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid
Inhibitors of Mitosis and Cell Division
benomyl, carbendazim, diethofencarb, ethaboxam, fuberidazole, pencycuron, thiabendazole, thiophanate-methyl, zoxamide
Inhibitors of Respiratory Chain Complex I
diflumctorim
Inhibitors of Respiratory Chain Complex II
boscalid, carboxin, fenfuram, flutolanil, furametpyr, furmecyclox, mepronil, oxycarboxin, penthiopyrad, thifluzamide
Decouplers
dinocap, fluazinam
Inhibitors of ATP Production
fentin acetate, fentin chloride, fentin hydroxide, silthiofam
Inhibitors of Amino Acid Biosynthesis and Protein Biosynthesis
andoprim, blasticidin-S, cyprodinil, kasugamycin, kasugamycin hydrochloride hydrate, mepanipyrim, pyrimethanil
Inhibitors of Signal Transduction
fenpiclonil, fludioxonil, quinoxyfen
Inhibitors of Lipid and Membrane Synthesis
chlozolinate, iprodione, procymidone, vinclozolin
ampropylfos, potassium-ampropylfos, edifenphos, etridiazole, iprobenfos (IBP), isoprothiolane, pyrazophos
tolclofos-methyl, biphenyl
iodocarb, propamocarb, propamocarb hydrochloride, propamocarb-fosetylate
Inhibitors of Ergosterol Biosynthesis
fenhexamid,
aldimorph, dodemorph, dodemorph acetate, fenpropidin, fenpropimorph, spiroxamine, tridemorph,
naftiftne, pyributicarb, terbinafine
Inhibitors of Cell Wall Synthesis
benthiavalicarb, bialaphos, dimethomorph, flumorph, iprovalicarb, mandipropamid, polyoxins, polyoxorim, validamycin A
Inhibitors of Melanin Biosynthesis
capropamid, diclocymet, fenoxanil, phthalide, pyroquilon, tricyclazole
Resistance Inductors
acibenzolar-S-methyl, probenazole, tiadinil
Multisite
captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram
Further Fungi Cides
amibromdol, benthiazole, bethoxazin, capsimycin, carvone, chinomethionat, chloropicrin, cufraneb, cyflufenamicl, cymoxanil, dazomet, debacarb, diclomezine, dichlorophen, dicloran, difenzoquat, difenzoquat metilsulphate, diphenylamine, ferimzone, flumetover, flusulfamide, fluoroimide, fosetylaluminium, fosetyl-calcium, fosetyl-sodium, hexachlorobenzene, 8-hydroxyquinoline sulphate, irumamycin, methasulfocarb, metrafenone, methyl isothiocyanate, mildiomycin, natamycin, nickel dimethyl dithiocarbamate, nitrothal-isopropyl, octhilinone, oxamocarb, oxyfenthiin, pentachloroplienol and salts, 2-phenylphenol and salts, piperalin, propanosine-sodium, proquinazid, pyribencarb, pyrrolnitrin, quintozene, tecloftalam, tecnazene, triazoxide, trichlamide, valiphenal, zarilamid,
2-(2-{[6-(3-chloro-2-methylphenoxy)-5-fluoropyrimidin-4-yl]oxy}phenyl)-2-(methoxyimino)-N-methylacetamide,
2-[[[[1-[3-(1-fluoro-2-phenylethyl)oxy]phenyl]ethylidene]amino]oxy]methyl]-alpha-(methoxyimino)-N-methyl-alpha-benzacetamide,
cis-1-(4-chlorophenyl)-2-(1H-1,2,4-triazol-1-yl)cycloheptanol,
1-[(4-methoxyphenoxy)methyl]-2,2-dimethylpropyl-1H-imidazole-1-carboxylic acid,
2,3,5,6-tetrachloro-4-(methylsulphonyl)pyridine,
2-butoxy-6-iodo-3-propylbenzopyranon-4-one,
2-chloro-N-(2,3-dihydro-1,1,3-trimethyl-1H-inden-4-yl)-3-pyridinecarboxamide,
3,4,5-trichloro-2,6-pyridinedicarbonitrile,
3,4-dichloro-N-(2-cyanophenyl)isothiazole-5-carboxamide (isotianil)
3-[5-(4-chlorophenyl)-2,3-dimethylisoxazolidin-3-yl]pyridine,
5-chloro-6-(2,4,6-trifluorophenyl)-N-[(1R)-1,2,2-trimethylpropyl][1,2,4]triazolo[1,5-a]pyrimidine-7-amine,
5-chloro-7-(4-methylpiperidin-1-yl)-6-(2,4,6-trifluorophenyl)[1,2,4]triazo[1,5-a]pyrimidine,
5-chloro-N-[(1R)-1,2-dimethylpropyl]-6-(2,4,6-trifluorophenyl)[1,2,4]triazolo[1,5-a]pyrimidine-7-amine,
methyl 2-[[[cyclopropyl[(4-methoxyphenyl)imino]methyl]thio]methyl]-alpha-(methoxymethylene)benzacetate,
methyl 1-(2,3-dihydro-2,2-dimethyl-1H-inden-1-yl)-1H-imidazole-5-carboxylate,
N-(3-ethyl-3,5,5-trimethylcyclohexyl)-3-formylamino-2-hydroxybenzamide,
N-(4-chloro-2-nitrophenyl)-N-ethyl-4-methylbenzene-sulphonamide,
N-(4-chlorobenzyl)-3-[3-methoxy-4-(prop-2-yn-1-yloxy)phenyl]propanamide,
N-[(4-chlorophenyl)(cyano)methyl]-3-[3-methoxy-4-(prop-2-yn-1-yloxy)phenyl]propanamide,
N-(5-bromo-3-chloropyridin-2-yl)methyl-2,4-dichloronicotinamide,
N-[1-(5-bromo-3-chloropyridin-2-yl)ethyl]-2,4-dichloronicotinamide,
(2S)-N-[2-[4-[[3-(4-chlorophenyl)-2-propynyl]oxy]-3-methoxyphenyl]ethyl]-3-methyl-2-[(methylsulphonyl)amino]butanamide,
N-{(Z)-[(cyclopropylmethoxy)imino][6-(difluoromethoxy)-2,3-difluorophenyl]methyl}-2-benzacetamide,
N-{2-[1,1'-bi(cyclopropyl)-2-yl]phenyl}-3-(difluoromethyl)-1-methyl-1H-pyrazole-4-carboxamide,
N-ethyl-N-methyl-N'-{2-methyl-5-(trifluoromethyl)-4-[3-(trimethylsilyl)propoxy]phenyl}-imidoformamide,
O-[1-[(4-methoxyphenoxy)methyl]-2,2-dimethylpropyl]-1H-imidazole-1-carbothioic acid,
2-amino-4-methyl-N-phenyl-5-thiazolecarboxamide,
2,4-dihydro-5-methoxy-2-methyl-4-[[[[1-[3-(trifluoromethyl)phenyl]ethylidene]amino]oxy]methyl]phenyl]-3H-1,2,4-triazol-3-one (CAS No. 185336-79-2),
N-(6-methoxy-3-pyridinyl)cyclopropanecarboxamide,
Bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
Acetylcholine Esterase (AChE) Inhibitors
Carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate
Organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormcphos, chlorpyrifos (-methyl/-ethyl), coumaphos, cyanofenphos, cyanophos, chlorfenvinphos, demeton-S-methyl, demeton-S-methylsulphone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydcmeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion
Sodium Channel Modulators/Voltage-Dependent Sodium Channel Blockers
Pyrethroids,
for example acrinathrin, allethrin (d-cis-trans, d-trans), beta-cyfluthrin, bifenthrin, bioallethrin, bioallethrin-5-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZX18901, pyrethrins (pyrethrum)
DDT
  Oxadiazines,
for example indoxacarb
  Semi carbazone,
for example metaflumizon (BAS3201)
Acetylcholine receptor agonists/antagonists
  Nicotine, bensultap, cartap
Acetylcholine receptor modulators
  Spinosyns,
for example spinosad, spinetoram
GABA-controlled chloride channel antagonists
  Orga-nochlorines,
for example camphechlor, chlordane, endosulfan, gamma-HCH, HCH, heptachlor, lindane, methoxychlor
  Fiprols,
for example acetoprole, pyrafluprole, pyriprole, vaniliprole
Chloride channel activators
Mectins,
for example abamectin, emamectin, emamectin benzoate, ivermectin, lepimectin, milbemycin
  Juvenile hormone mimetics,
for example diofenolan, epofenonane, fenoxycarb, hydroprene, kinoprene, methoprene, pyriproxifen, triprene
Ecdysone agonists/disruptors
  Diacylhydrazines,
for example chromafenozide, halofenozide, methoxyfenozide, tebufenozide
Chitin Biosynthesis Inhibitors
  Benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
  Buprofezin
  Cyromazine
Oxidative phosphorylation inhibitors, ATP disrupters
  Diafenthiuron
  Organotin compounds,
for example azocyclotin, cyhexatin, fenbutatin oxide
Oxidative phosphorylation decouplers acting by interrupting the H-proton gradient
  Pyrroles,
for example chlorfenapyr
  Dinitrophenols,
for example binapacyrl, dinobuton, dinocap, DNOC, meptyldinocap
Site-1 electron transport inhibitors
  METIs,
for example fenazaquin, fenpyroximate, pyrimidifen, pyridaben, tebufenpyrad, tolfenpyrad
  Hydramethylnon
  Dicofol
Site-II electron transport inhibitors
  Rotenone
Site-III electron transport inhibitors
  Acequinocyl, fluacrypyrim
Microbial disrupters of the insect gut membrane
*Bacillus thuringiensis* strains
Lipid synthesis inhibitors
  Tetramic acids,
for example cis-3-(2,5-dimethylphenyl)-4-hydroxy-8-methoxy-1-azaspiro[4.5]dec-3-en-2-one
  Carboxamides,
for example flonicamid
  Octopaminergic agonists,
for example amitraz
  Inhibitors of magnesium-stimulated ATPase,
Propargite
  Nereistoxin analogues,
for example thiocyclam hydrogen oxalate, thiosultap-sodium
Ryanodine receptor agonists,
  Benzodicarboxamides,
for example flubendiamide
  Anthranilamides,
for example Rynaxypyr (3-bromo-N-{4-chloro-2-methyl-6-[(methylamino)carbonyl]phenyl}-1-(3-chloropyridin-2-yl)-1H-pyrazole-5-carboxamide)

Biologicals, Hormones or Pheromones azadirachtin, *Bacillus* spec., *Beauveria* spec., codlemone, *Metarrhizium* spec, *Paecilomyces* spec, thuringiensira, *Verticillium* spec.

Active compounds with unknown or unspecific mechanisms of action

Fumigants, for example aluminium phosphide, methyl bromide, sulphuryl fluoride

Antifeedants, for example cryolite, flonicamid, pymetrozine

Mite growth inhibitors, for example clofentezine, etoxazole, hexythiazox

Amidoflumet, benclothiaz, benzoximate, bifenazate, bromopropylate, buprofezin, chinomethionat, chlordimeform, chlorobenzilate, chloropicrin, clothiazoben, cycloprene, cyflumetofent, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as fertilizers, growth regulators, semiochemicals, or else with agents for improving the plant properties, is also possible.

Compositions of the invention may further comprise, as well as at least one compound of the formula (I), at least one further active herbicidal ingredient, preferably from the group consisting of acetochlor, acifluorfen (-sodium), aclonifen, alachlor, alloxydim (-sodium), ametryne, amicarbazone, amidochlor, amidosulphuron, aminopyralid, anilofos, asulam, atrazine, azafenidin, azimsulphuron, beflubutamid, benazolin (-ethyl), benzcarbazone, benfuresate, bensulphuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulphuron, chlortoluron, cinidon (-ethyl), cinmethylin, cinosulphuron, clefoxydim, clethodim, clodinafop (-propargyl), clomazone, clomeprop, clopyralid, clopyrasulphuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulphuron (-methyl), ethofumesate, ethoxyfen, ethoxysulphuron, etobenzanid, fenoxaprop (—P-ethyl), fentrazamide, flamprop (-isopropyl, -isopropyl-L, -methyl), flazasulphuron, florasulam, fluazifop (—P-butyl), fluazolate, flucarbazone (-sodium), flucetosulphuron, flufenacet, flufenpyr, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulphuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, glufosinate (-ammonium), glyphosate (-isopropylammonium), halosafen, haloxyfop (-ethoxyethyl, —P-methyl), hexazinone, HOK-201, imazamethabenz (-methyl), imazamethapyr, imazamox, imazapic, imazapyr, imazaquin, imazethapyr, imazosulphuron, ioxynil, isopropalin, isoproturon, isouron, isoxaben, isoxachlortole, isoxaflutole, isoxapyrifop, KIH 485, lactofen, lenacil, linuron, MCPA, mecoprop, rnefenacet, metamifop, metamitron, metazachlor, methabenzthiazuron, metobenzuron, metobromuron, (alpha-) metolachlor, metosulam, metoxuron, metribuzin, metsulphuron (-methyl), molinate, monolinuron, naproanilide, napropamide, neburon, nicosulphuron, norflurazon, orbencarb, orthosulfamuron, oryzalin, oxadiargyl, oxadiazon, oxasulphuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulphuron (-methyl), profluazol, prometryn, propachlor, propanil, propaquizafop, propisochlor, propoxycarbazone (-sodium), propyzamide, prosulfocarb, prosulphuron, pyraflufen (-ethyl), pyrazogyl, pyrazolate, pyrazosulphuron (-ethyl), pyrazoxyfen, pyribenzoxim, pyributicarb, pyridate, pyridatol, pyriftalid, pyriminobac (-methyl), pyrithiobac (-sodium), pyrimisulfan, quinchlorac, quinmerac, quinoclamine, quizalofop (—P-ethyl, —P-tefuryl), rimsulphuron, sethoxydim, simazine, simetryn, sulfentrazone, sulfometuron (-methyl), sulfosate, sulfosulphuron, tebutam, tebuthiuron, tepraloxydim, terbuthylazine, terbutryn, TH-547, thenylchlor, thiafluamide, thiazopyr, thidiazimin, thifensulphuron (methyl), thiobencarb, thiocarbazil, topramezone, tralkoxydim, triallate, triasulphuron, tribenuron (-methyl), triclopyr, tridiphane, trifluralin, trifloxysulphuron, triflusulphuron (-methyl), tritosulphuron and triflosulam.

When used, the compositions according to the invention can furthermore be present in their commercially available formulations and in the use forms, prepared from these formulations, as a mixture with synergistic agents. Synergistic agents are compounds which increase the action of the active compounds present in the compositions according to the invention, without it being necessary for the synergistic agent added to be active itself.

When used, the compositions according to the invention can furthermore be present in their commercially available formulations and in the use forms, prepared from these formulations, as mixtures with inhibitors which reduce degradation of the agrochemically active compound present after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional breeding and optimization methods or by biotechnological and genetic engineering methods or by combinations of these methods, including the transgenic plants and including the plant cultivars which can or cannot be protected by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits and seeds, as well as roots, tubers and rhizomes. The plant parts also include harvested material, and vegetative and generative propagation material, for example cuttings, tubers, rhizomes, offshoots and seeds.

Treatment according to the invention of the plants and plant parts with the compositions is carried out directly or by action on their environment, habitat or storage space using customary treatment methods, for example by dipping, spraying, evaporating, atomizing, broadcasting, spreading-on, injecting and, in the case of propagation material, in particular in the case of seeds, furthermore by coating with one or more layers.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particular advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean). Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compositions according to the invention. The preferred ranges stated above for the compositions also apply to the treatment of these plants. Particular emphasis is given to the treatment of plants with the compositions specifically mentioned in the present text.

The compositions according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compositions according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the compositions according to the invention.

The compositions according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the compositions can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the insecticidal compositions according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens. Trogoxylon aequale, Minthes rugicollis, Xyleborus* spec. *Tryptodendron* spec. *Apate monachus, Bostryehus capucins, Heterobostrychus brunneus, Sinoxylon* spec. *Dinoderus minutus;*

Hymenopterons, such as *Sirex juvencus, Urocerus gigas, Urocerus gigastaignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood, processed wood products and coating compositions.

The ready-to-use compositions may, if appropriate, comprise further insecticides and, if appropriate, one or more fungicides.

With respect to possible additional mixing partners, reference may be made to the insecticides and fungicides mentioned above.

The compositions according to the invention can likewise be employed for protecting objects which come into contact with seawater or brackish water, in particular hulls, screens, nets, buildings, moorings and signalling systems, against fouling.

Furthermore, the compositions according to the invention, alone or in combination with other active compounds, may be employed as antifouling agents.

In domestic, hygiene and stored-product protection, the compositions are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Tronibicula alfreddugesi, Neutrombicula autumnalis, Dermatophagoides pteronissimus, Dermatophagoides forinae.*

From the order of the Araneae, for example, *Avicularildae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Prilebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella. Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used as aerosols, pressureless spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

When the compositions according to the invention comprise at least one fungicidally active compound, they have very good fungicidal properties and can be used for controlling phytopathogenic fungi, such as Plasmodiophoromycetes, Oomycetes, Chytridiomycetes, Zygomycetes, Ascomycetes, Basidiomycetes, Deuteromycetes, etc.

Some pathogens causing fungal diseases which come under the generic names listed above may be mentioned as examples, but not by way of limitation:

Diseases caused by powdery mildew pathogens, such as, for example,

*Blumeria* species, such as, for example, *Blumeria graminis;*
*Podosphaera* species, such as, for example, *Podosphaera leucotricha;*
*Sphaerothecat* species, such as, for example, *Sphaerotheca fuliginea;*
*Uncinula* species, such as, for example, *Uncinula necator;*

Diseases caused by rust disease pathogens, such as, for example,

*Gymnosporangium* species, such as, for example, *Gymnosporangium sabinae*
*Hemileia* species, such as, for example, *Hemileia vastatrix;*
*Phakopsora* species, such as, for example, *Phakopsora pachyrhizi* and *Phakopsora meibomiae;*
*Puccinia* species, such as, for example, *Puccinia recondita* or *Puccinia triticina;*
*Uronryces* species, such as, for example, *Uromyces appendiculatus;*

Diseases caused by pathogens from the group of the Oomycetes, such as, for example,

*Bremia* species, such as, for example, *Bremia lactucae;*
*Peronospora* species, such as, for example, *Peronospora pisi* or *P. brassicae;*
*Phytophthora* species, such as, for example *Phytophthora infestans;*
*Plasmopara* species, such as, for example, *Plasmopara viticola;*
*Pseudoperonospora* species, such as, for example, *Pseudoperonospora humuli* or *Pseudoperonospora cubensis;*
*Pythium* species, such as, for example, *Pythium ultimum;*

Leaf blotch diseases and leaf wilt diseases caused, for example, by

*Alternaria* species, such as, for example, *Alternaria solani;*
*Cercospora* species, such as, for example, *Cercospora beticola;*
*Cladiosporium* species, such as, for example, *Cladiosporium cucumerinum;*
*Cochliobolus* species, such as, for example, *Cochliobolus sativus*
(conidia form: *Drechslera*, Syn: *Helminthosporium*);
*Colletotrichum* species, such as, for example, *Colletotrichum lindemuthanium;*
*Cycloconium* species, such as, for example, *Cycloconium oleaginum;*
*Diaporthe* species, such as, for example, *Diaporthe citri;*
*Elsinoe* species, such as, for example, *Elsinoe fawcettii;*
*Gloeosporium* species, such as, for example, *Gloeosporium laeticolor;*
*Glomerella* species, such as, for example, *Glomerella cingulata;*
*Guignardia* species, such as, for example, *Guignardia bidwelli;*
*Leptosphaeria* species, such as, for example, *Leptosphaeria maculans;*
*Magnaporthe* species, such as, for example, *Magnaporthe grisea;*
*Mycosphaerella* species, such as, for example, *Mycosphaerella graminicola;*
*Phaeosphaeria* species, such as, for example, *Phaeosphaeria nodorum;*
*Pyrenophora* species, such as, for example, *Pyrenophora teres;*
*Ramularia* species, such as, for example, *Ramularia collocygni;*
*Rhynchosporium* species, such as, for example, *Rhynchosporium secalis;*
*Septoria* species, such as, for example, *Septoria apii;*
*Typhula* species, such as, for example, *Typhula incarnata;*
*Venturia* species, such as, for example, *Venturia inaequalis;*

Root and stem diseases caused, for example, by

*Corticium* species, such as, for example, *Corticium graminearum;*

*Fusarium* species, such as, for example, *Fusarium oxysporum;*
*Gaeumannormyces* species, such as, for example, *Gaeumannomyces graminis;*
*Rhizoctonia* species, such as, for example *Rhizoctonia solani;*
*Tapesia* species, such as, for example, *Tapesia acuformis;*
*Thielaviopsis* species, such as, for example, *Thielaviopsis basicola;*
Ear and panicle diseases (including maize cobs) caused, for example, by
*Alternaria* species, such as, for example, *Alternaria* spp.;
*Aspergillus* species, such as, for example, *Aspergillus flavus;*
*Cladosporium* species, such as, for example, *Cladosporium* spp.;
*Claviceps* species, such as, for example, *Claviceps purpurea;*
*Fusarium* species, such as, for example, *Fusarium culmorum;*
*Gibberella* species, such as, for example, *Gibberella zeae;*
*Monographella* species, such as, for example, *Monographella nivalis;*
Diseases caused by smut fungi, such as, for example,
*Sphacelotheca* species, such as, for example, *Sphacelotheca reiliana;*
*Tilletia* species, such as, for example, *Tilletia caries;*
*Urocystis* species, such as, for example, *Urocystis occulta;*
*Ustilago* species, such as, for example, *Ustilago nuda;*
Fruit rot caused, for example, by
*Aspergillus* species, such as, for example, *Aspergillus flavus;*
*Botrytis* species, such as, for example, *Botrytis cinerea;*
*Penicillium* species, such as, for example, *Penicillium expansum;*
*Sclerotinia* species, such as, for example, *Sclerotinia sclerotiorum;*
*Verticilium* species, such as, for example, *Verticilium alboatrum;*
Seed- and soil-borne rot and wilt diseases, and also diseases of seedlings, caused, for example, by
*Fusarium* species, such as, for example, *Fusarium culmorum;*
*Phytophthora* species, such as, for example, *Phytophthora cactorum;*
*Pythium* species, such as, for example, *Pythium ultimum;*
*Rhizoctonia* species, such as, for example, *Rhizoctonia solani;*
*Sclerotium* species, such as, for example, *Sclerotium rolfsii;*
Cancerous diseases, galls and witches' broom caused, for example, by
*Nectria* species, such as, for example, *Nectria galligena;*
Wilt diseases caused, for example, by
*Monilinia* species, such as, for example, *Monilinia laxa;*
Deformations of leaves, flowers and fruits caused, for example, by
*Taphrina* species, such as, for example, *Taphrina deformans;*
Degenerative diseases of woody plants caused, for example, by
*Esca* species, such as, for example, *Phaemoniella clamydospora;*
Diseases of flowers and seeds caused, for example, by
*Botiytis* species, such as, for example, *Botrytis cinerea;*
Diseases of plant tubers caused, for example, by
*Rhizoctonia* species, such as, for example, *Rhizoctonia solani;*
Diseases caused by bacteriopathogens, such as, for example,
*Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora.*

Preference is given to controlling the following diseases of soya beans:
fungal diseases on leaves, stems, pods and seeds caused, for example, by
alternaria leaf spot (*Alternaria* spec, atrans tenuissima), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera* trispora (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerutlina leaf spot (*Leptosphaerulina trifolii*), phyllosticta leaf spot (*Phyllosticta sojaecola*), powdery mildew (*Microsphaera diffusa*), pyrenochaeta leaf spot (*Pyrenochaeta glycines*), rriizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base caused, for example, by
black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megaspenna*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The compositions according to the invention comprising at least one herbicidally active compound (=herbicidal compositions) have excellent herbicidal activity against a broad spectrum of economically important mono- and dicotyledonous harmful plants. In this context, it is immaterial whether the substances are applied pre-sowing, pre-emergence or post-emergence.

By way of example, specific mention may be made of some representatives of the mono- and dicotyledonous weed flora which can be controlled by the compounds according to the invention; however, this list is not to be understood as meaning a limitation to certain species.

Among the monocotyledonous grass species, the compounds act efficiently, for example, both against self-sown cereals, such as wheat, barley, rye and triticale, and, for example, against *Apera spica* venti, *Avena* spp., *Alopecurus* spp., *Brachiaria* spp., *Digitaria* spp., *Lolium* spp., *Echinochloa* spp., *Panicurn* spp., *Phalaris* spp., *Poa* spp., *Setaria* spp. and also *Bromus* spp., such as *Bromus catharticus, Bromus secalinus, Bromus erectus, Bromus tectorum* and *Bromus japonicus*, and *Cyperus* species from the annual group and, from among the perennial species, *Agropyron, Cynodon, Imperata* and *Sorghum*, and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., *Papaver rhoeas* spp., *Centaurea* spp. among the annual species, and also *Convolvulus, Cirsium, Rumex* and *Artemisia* spp. among the perennial weeds.

If the herbicidal compositions according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

The herbicidal compositions according to the invention are distinguished by a rapid and long-lasting herbicidal action. The shower resistance of the active compounds in the combinations according to the invention is generally favourable. By using the active compound combination according to the invention, it is possible to reduce the required application rate of the active compounds considerably.

The herbicidal compositions according to the invention have excellent herbicidal activity against a broad spectrum of economically important monocotyledonous and dicotyledonous harmful plants including species resistant against herbicidally active compounds such as glyphosate, glufosinate, atrazine or imidazolinone herbicides.

Although the herbicidal compositions according to the invention have an excellent herbicidal activity against monocotyledonous and dicotyledonous harmful plants, the crop plants are not damaged at all, or only to a negligible extent.

In addition, the compositions according to the invention in some cases have outstanding growth-regulating properties in crop plants. They engage in the plant metabolism in a regulating manner and can thus be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledonous and dicotyledonous crops because lodging can be reduced hereby, or prevented completely.

By virtue of their herbicidal and plant growth-regulatory properties, the compositions according to the invention can be employed for controlling harmful plants in crop plants which are genetically modified or have been obtained by mutation/selection. These crop plants generally have particularly advantageous properties, for example resistance to herbicidal compositions or plant diseases or causative organisms of plant diseases, such as certain insects or microorganisms such as fungi, bacteria or viruses. Other particular properties relate, for example, to the quantity, quality, storage-stability, composition and specific ingredients of the harvested product. Thus, for example, transgenic plants having an increased starch content or a modified quality of the starch or those having a different fatty acid composition of the harvested product are known.

Conventional ways of preparing novel plants which have modified properties compared to known plants comprise, for example, traditional breeding methods and the generation of mutants (see, for example, U.S. Pat. No. 5,162,602; U.S. Pat. No. 4,761,373; U.S. Pat. No. 4,443,971). Alternatively, novel plants having modified properties can be generated with the aid of genetic engineering methods (see, for example, EP-A-0 221 044, EP-A-0 131 624). For example, there have been described several cases of genetically engineered changes in crop plants in order to modify the starch synthesized in the plants (for example WO 92/11376, WO 92/14827, WO 91/19806),
   transgenic crop plants which are resistant to other herbicides, for example sulphonylureas (EP-A-0 257 993, U.S. Pat. No. 5,013,659), to glyphosate (Round-up Ready© cultivars), to glufosinate (LibertyLink© cultivars) or to imidazolinones,
   transgenic oilseed rape plants, for example imidazolinone-resistant oilseed rape cultivars, Roundup Ready© oilseed rape (RJR-oilseed rape) or LibertyLink© oilseed rape (LL-oilseed rape),
   transgenic crop plants having the ability to produce *Bacillus thuringiensis* toxins (Bt toxins) which make the plants resistant to certain pests (EP-A-0 142 924, EP-A-0 193 259),
   transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd Ed., Cold Spring Harbor Laboratory Press, Cold Spring Harbor, NY; or Winnacker "Gene und Klone" [Genes and Clones], VCH Weinheim, 2nd Edition 1996, or Christou, "Trends in Plant Science" 1 (1996) 423-431).

In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cell. However, to achieve localization in a certain compartment, it is possible, for example, to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

Furthermore, the present invention also provides a method for controlling unwanted vegetation (for example harmful plants), preferably in crop plants such as cereals (for example wheat, barley, rye, oats, crossbreeds thereof, such as triticale, rice, corn, millet), sugar beet, sugar cane, oilseed rape, cotton and soya bean, particularly preferably in monocotyledonous crops such as cereals, for example wheat, barley, rye, oats, crossbreeds thereof, such as triticale, rice, corn and millet, or in dicotyledonous crops, which method comprises applying one or more herbicides of type (A) and one or more herbicides of type (B) jointly or separately, for example by the pre-emergence method, the post-emergence method or the pre- and post-emergence method, to the plants, for example harmful plants, parts of plants, plant seed or the area on which the plants grow, for example the area under cultivation.

The crop plants may also be genetically modified or obtained by mutation/selection.

The herbicidal compositions according to the invention can also be employed non-selectively for controlling unwanted vegetation, for example in plantation crops, on roadsides, squares, industrial sites or railway tracks.

The preparation and use examples below illustrate the invention without limiting it in any way.

PREPARATION EXAMPLES

To prepare a suspension concentrate, initially all liquid components are mixed with one another. In the next step, the solids are added and the mixture is stirred until a homogeneous suspension is formed. The homogeneous suspension is subjected initially to coarse grinding and then to fine grinding, resulting in a suspension in which 90% of the solids particles have a particle size below 10 µm. Subsequently, Kelzan® S and water are added at room temperature with stirring. This gives a homogeneous suspension concentrate.

TABLE 1

Compositions of formulations according to the invention (in % by weight)

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Imidacloprid | | | | | 21.6 | | | | 4.4 | 11 | |
| Spirotetramate | 4.5 | 4.6 | 11 | 18.7 | | | 13.4 | 14.9 | 4.4 | 11 | |
| Tebuconazole | | | | | | | | | | | 17.8 |
| Thiacloprid | | | | | | 18.7 | 8.9 | 7.4 | | | |
| Atlox ® 4913 | | | | | 4.5 | | 3 | 3 | 3 | 3 | 2.7 |
| Crovol ® CR 70 G | 15 | 20 | 20 | 10 | 15 | 10 | 15 | 15 | 20 | 20 | 15 |
| Emulgator PS ® 29 | 4 | 4 | 4 | 4 | | 4 | | | | | |
| Emulgator PS ® 54 | | | | | 1.5 | | 5 | 5 | 3 | 3 | 1.5 |
| Glycerol | 10 | 10 | 10 | 10 | 10 | 10 | 10 | 10 | 10 | 10 | 10 |
| Kelzan ® S | 0.3 | 0.2 | 0.1 | 0.2 | 0.1 | 0.2 | 0.2 | 0.2 | 0.4 | 0.4 | 0.1 |
| Morwet ® D 425 | | | | | | | | | | | 0.5 |
| Preventol ® D7 | 0.08 | 0.08 | 0.08 | 0.08 | 0.08 | 0.08 | 0.08 | 0.08 | 0.08 | 0.08 | 0.08 |
| Proxel ® GXL | 0.12 | 0.12 | 0.12 | 0.12 | 0.12 | 0.12 | 0.12 | 0.12 | 0.12 | 0.12 | 0.12 |
| Silfoam ® SRE | 0.1 | 0.1 | 0.1 | 0.1 | 0.1 | 0.1 | 0.1 | 0.1 | 0.1 | 0.1 | 0.1 |
| Citric acid | 0.1 | 0.1 | 0.1 | 0.1 | 0.1 | 0.1 | 0.1 | 0.1 | 0.1 | 0.1 | 0.1 |
| Water | 65.8 | 60.8 | 54.5 | 56.7 | 46.9 | 56.7 | 44.1 | 44.1 | 54.4 | 41.2 | 52 |

Storage Stability of the Formulations According to the Invention

To examine the storage stability, 100 ml of formulation were stored under changing temperature conditions (TW) and at 54° C. for eight weeks. The changing temperature conditions are 48 hours at 30° C., reduction of the temperature over 22.5 hours at 2° C./hour to −15° C., 75 hours at −15° C., increase of the temperature over 22.5 hours at 2° C./hour to 30° C. After storage, the sample is brought to room temperature, and dispersibility, particle size and viscosity are checked.

The dispersibility (DISP) is determined according to the CIPAC MT 180 method, the particle size (d90, Part) is measured on a Malvern Mastersizer 2000, and the dynamic viscosity (Visc) is measured at 20 s$^{-1}$ using a RheoStress RS 150 from Haake.

TABLE 2

Storage stability of formulations according to the invention

| | Original value | | | 8 weeks at 54° C. | | | 8 weeks TW | | |
|---|---|---|---|---|---|---|---|---|---|
| | DISP in % | Part in µm | Visc/ mPas | DISP in % | Part in µm | Visc/ mPas | DISP in % | Part in µm | Visc/ mPas |
| Example 1 | 0.1 | 4.2 | 202 | 0.1 | 5.6 | 174 | 0.1 | 4.4 | 193 |
| Example 2 | 0.1 | 3.7 | 308 | 0.1 | 4.5 | 265 | 0.1 | 3.6 | 289 |

TABLE 2-continued

Storage stability of formulations according to the invention

|  | Original value | | 8 weeks at 54° C. | | | 8 weeks TW | | |
| --- | --- | --- | --- | --- | --- | --- | --- | --- |
|  | DISP in % | Part in μm | Visc/ mPas | DISP in % | Part in μm | Visc/ mPas | DISP in % | Part in μm | Visc/ mPas |
| Example 3 | 0 | 3.8 | 308 | 0 | 4.5 | 265 | 0 | 3.6 | 289 |
| Example 4 | 0.1 | 3.6 | 480 | 0.1 | 4.3 | 434 | 0.1 | 3.7 | 468 |
| Example 5 | 0.1 | 3.1 | 583 | 0.1 | 4.6 | 261 | 0.1 | 5 | 282 |
| Example 6 | 0.1 | 3.0 | 317 | 0.1 | 4.9 | 261 | 0.1 | 5.5 | 281 |
| Example 7 | 0.1 | 3.6 | 786 | 0.1 | 3.6 | 712 | 0.1 | 3 | 791 |
| Example 8 | 0.1 | 3.1 | 583 | 0.1 | 3.7 | 435 | 0.1 | 3 | 523 |
| Example 9 | 0 | 2.7 | 526 | 0.1 | 3.3 | 344 | 0.1 | 2.5 | 436 |
| Example 10 | 0 | 2.8 | 193 | 0.1 | 7.1 | 365 | | | |
| Example 11 | | | | | | | | | |

Determination of the Static Surface Tension

Surface tens ion of the penetrants according to the invention at 0.5 g/l in tap water and at room temperature measured using a Krüss tensiometer K100 Wilhelmy plate method in accordance with ASTM D 1331-56.

TABLE 3

Surface tension of the penetrants according to the invention

| Penetrant | Surface tension in mN/m at 20-22° C. |
| --- | --- |
| Crovol ® CR70G | 44.7 |
| Crovol ® M70 | 43.7 |
| Crovol ® A7OUK | 42.0 |
| Crovol ® PK70 | 40.4 |
| Agrimul ® RSO 1503 | 45.9 |
| Agrimul ® RSO 4003 | 41.8 |
| Water | 72.0 |

Determination of the Plant Compatibility of Various Adjuvants

Plant compatibility of the penetrants (on their own) at 0.5 g/l in tap water on sensitive leaves of miniroses. Plants in a climatized cabinet at 20° C./60% atmospheric humidity during the day and 18° C./70% atmospheric humidity at night.

TABLE 4

Plant compatibility of various adjuvants

| Penetrant | Necroses on rose leaves* after 1 day | Necroses on rose leaves* after 5 days |
| --- | --- | --- |
| According to the invention | | |
| Crovol ® CR70G | 0 | 0 |
| Crovol ® M70 | 0 | 0 |
| Crovol ® A7OUK | 0 | 0 |
| Crovol ® PK70 | 0 | 0 |
| Agrimul ® RSO 1503 | 0 | 1 |
| Agrimul ® RSO 4003 | 1 | 0 |
| Comparative | | |
| Genapol ® C100 (alcohol ethoxylate) | 2 | 2 |
| Etocas ® 10 (castor oil ethoxylate) | 1 | 1 |

*0 = no necrosis; 1 = slight spot-like necrosis on the leaf area wetted by the drop, 2 = ring-shaped necrosis, 3 = maximally extended necrosis Depending on the penetrant, 4×10 μl drops were applied to the upper side of a leaf, in each case two on the two halves of the leaf as defined by the central axis. A number of leaves of the same plant were used. Moreover, as an internal standard for a typical reaction of the leaf, Genapol C-100 was applied to the front third of the leaf, resulting in a ring-shaped necrosis. Application and drying were carried out at a relative atmospheric humidity of 30-40% and a temperature of ~21° C.

Evaluation was carried out visually using an evaluation template. Furthermore, photos were taken with a digital camera. To exclude the possibility that spray coatings are identified as damage, all application sites were stripped with cellulose acetate and an additional scoring was carried out after removal of the spray coating.

Determination of the Plant Compatibility of Various Spirotetramate/Adjuvant Combinations Plant compatibility of spray liquors comprising the insecticide spirotetramate (0.2 g/l) with the penetrants at 0.5 g/l in tap water on bell pepper leaves (*Capsicum annuum* cv. Pusta Gold). Plants in a climatized cabinet at 20° C./60% atmospheric humidity during the day and 18° C./70% atmospheric humidity at night.

TABLE 5

Plant compatibility of spirotetramate

| BY18330 (0.2 g/l) + penetrant (0.5 g/l) | Necroses on bell pepper leaves* after 1 day | Necroses on bell pepper leaves* after 6 days |
| --- | --- | --- |
| According to the invention | | |
| Crovol ® CR70G | 0 | 0 |
| Crovol ® M70 | 0 | 0 |
| Crovol ® A7OUK | 0 | 0 |
| Crovol ® PK70 | 0 | 0 |
| Agrimul ® RSO 1503 | 0 | 1 |
| Agrimul ® RSO 4003 | 1 | 0 |
| Comparative | | |
| Genapol ® C100 | 1 | 3 |
| Etocas ® 10 | 0 | 2 |

*0 = no necrosis; 1 = slight spot-like necrosis on the leaf area wetted by the drop, 2 = ring-shaped necrosis, 3 = maximally extended necrosis Depending on the penetrant, 2×10 μl drops were applied in each case once to both halves of the leaf as defined by the central axis. A plurality of penetrants were applied to one leaf (upper side) and a number of leaves of the same plant were used. Moreover, as an internal standard for a typical reaction of the leaf, Genapol C-100 was applied to the front third of the leaf, resulting in a ring-shaped necrosis. Application and drying were carried out at a relative atmospheric humidity of 30-40% and a temperature of ~21° C.

Evaluation was carried out visually using an evaluation template. Furthermore, photos were taken with a digital camera. To exclude the possibility that spray coatings are identified as damage, all application sites were stripped with cellulose acetate and an additional scoring was carried out after removal of the spray coating.

Determination of the Plant Compatibility of Various Tebuconazole/Penetrant Combinations Plant compatibility on soya bean leaves of tebuconazole formulated as WG with rapeseed oil methyl ester penetrant (Mero®) and Crovol® CR70G.

TABLE 6

Plant compatibility of tebuconazole

| Tebuconazole (0.5 g/l) + penetrant (1 or 3 g/l) | Necroses on soya bean leaves* after 1 day | Necroses on soya bean leaves* after 5 days |
|---|---|---|
| Comparative | | |
| +Mero ® (1 g/l) | 3 | 3 |
| +Mero ® (3 g/l) | 3 | 3 |
| According to the invention | | |
| Crovol ® CR70G (1 g/l) | 0 | 0 |
| Crovol ® CR70G (3 g/l) | 0 | 0 |

*0 = no necrosis; 1 = slight spot-like necrosis on the leaf area wetted by the drop, 2 = ring-shaped necrosis, 3 = maximally extended necrosis Depending on the penetrant, 2×10 µl drops were applied to the leaf, in each case to both halves of the leaf as defined by the central axis. A plurality of penetrants were applied to one leaf (upper side) and a number of leaves of the same plant were used. Application and drying were carried out at a relative atmospheric humidity of 30-40% and a temperature of ~21° C.

Evaluation was carried out visually using an evaluation template. Furthermore, photos were taken with a digital camera. To exclude the possibility that spray coatings are identified as damage, all application sites were stripped with cellulose acetate and an additional scoring was carried out after removal of the spray coating.

Determination of the Cuticle Penetration of Various Spirotetramate/Penetrant Combinations Penetration* of spirotetramate with penetrants according to the invention compared to the control without penetrant and the rapid-action uptake enhancer Genapol® X150. All penetrants employed at 0.5 g/l.

TABLE 7

Uptake of spirotetramate by apple leaf cuticles

| Penetrant | % penetration after 24 h** | % penetration after 3 days** |
|---|---|---|
| Control (without addit.) | 0.1 | 0.3 |
| Genapol ® X150 | 39.2 | 72 (after 2 days) |
| Crovol ® CR70G | 5.8 | 40.5 |
| Crovol ® M70 | 12.4 | 62.5 |
| Crovol ® A7OUK | 11 | 53.7 |
| Crovol ® PK70 | 4.1 | 15.4 |
| Agrimul ® RSO 1503 | 2.9 | 13.2 |
| Agrimul ® RSO 4003 | 3.1 | 15.8 |
| Etocas ®*** 10 | 1.7 | 9.9 |
| Etocas ®*** 35 | 0.9 | 7.8 |

*Active compound dissolved at 0.2 g/l in a mixture of acetone/tap water (20/80)
**Mean values from 4-8 repetitions for penetration through apple leaf cuticles (T = 20° C., rel. atmospheric humidity 56%)
***castor oil ethoxylate This test measured the penetration of active compounds through enzymatically isolated cuticles of apple leaves.

The leaves used were cut in the fully developed state from apple trees of the Golden Delicious variety. The cuticles were isolated as follows:

first of all, leaf discs labelled on the underside with dye and formed by punching were filled by means of vacuum infiltration with a pectinase solution (0.2% to 2% strength) buffered to a pH of between 3 and 4, then sodium azide was added and the leaf discs thus treated were left to stand until the original leaf structure broke down and the non-cellular cuticles underwent detachment.

Thereafter only those cuticles from the top leaf sides that were free from stomata and hairs were used further. They were washed a number of times in alternation with water and with a buffer solution, pH 7. The clean cuticles obtained were, finally, applied to Teflon plaques and smoothed and dried with a gentle jet of air.

In the next step the cuticular membranes obtained in this way were placed in stainless steel diffusion cells (transport chambers) for the purpose of membrane transport investigations. For these investigations the cuticles were placed centrally using tweezers on the edges of the diffusion cells, which were coated with silicone grease, and sealed with a ring, which was likewise greased. The arrangement was chosen so that the morphological outer side of the cuticles was directed outwards, in other words to the air, while the original inner side was facing the interior of the diffusion cell.

The diffusion cells were filled with a 1% phospholipid suspension. Penetration was determined by applying in each case 10 µl of the spray liquor of the composition below, containing radiolabeled active compound in the stated concentrations, to the outer face of the cuticles. The spray liquor is prepared using local tap water of average hardness.

After the spray liquors had been applied, the water was evaporated and then the chambers were inverted and placed in thermostatted troughs, in which the temperature and air humidity over the cuticles was adjustable by means of a gentle air stream onto the cuticles with the spray coating (20° C., 60% rh). At regular intervals, an autosampler took aliquots which were subjected to measurement in a scintillation counter.

Determination of the Cuticle Penetration of Various Active Compound/Penetrant Combinations Facilitation of the penetration of various active compounds* by penetrants according to the invention exemplified by Crovol® CR70G in comparison to the control.

TABLE 8

Uptake of various active compounds by apple leaf cuticles

| Active compound without/ with Crovol ®CR70G | % penetration (after hours)** | % penetration (after hours)** |
|---|---|---|
| Spirotetramarte without | 0.1 (24) | 0.3 (72) |
| Spirotetramarte with 0.5 g/l Crovol ® CR70G | 5.8 (24) | 40.5 (72) |
| Tebuconazole without | <2 (24) | <2 (72) |
| Tebuconazole with 0.5 g/l Crovol ® CR70G | 6.0 (24) | 31.5 (72) |
| Tembotrione without | <1 (6) | <1 (18) |
| Tembotrione with 1.0 g/l Crovol ® CR70G | 3.7 (6) | 11.2 (18) |
| Fluopicolide without | 0.8 (24) | 2.8 (48) |
| Fluopicolide with 0.5 g/l Crovol ® CR70G | 4.1 | 12.3 |

TABLE 8-continued

Uptake of various active compounds by apple leaf cuticles

| Active compound without/<br>with Crovol ®CR70G | % penetration (after hours)** | % penetration (after hours)** |
|---|---|---|
| Imidacloprid without | 0.7 (24) | 2.2 (48) |
| Imidacloprid with 0.45 g/l Crovol ® CR70G (i.e. 30% strength absorbate for WG) | 31.1 (24) | 58.3 (48) |

*Active compounds dissolved at concentrations of 0.1-0.5 g/l in water or a mixture of acetone/tap water (20/80)
**Mean values from 4-8 repetitions for penetration through apple leaf cuticles (T = 20-25° C., rel. atmospheric humidity 56-60%)

The invention claimed is:

1. A composition in the form of a water-based suspension concentrate, comprising
   (a) from 1 to 60% by weight of at least one active compound, wherein said at least one active compound is spirotetramate,
   (b) from 1 to 20% by weight of a penetrant selected from the group consisting of an ethoxylate of rapeseed oil,
   (c) from 1 to 20% by weight of at least one nonionic and/or at least one anionic surfactant,
   (d) from 0.1 to 25% by weight of at least one additive selected from the group consisting of antifoams, preservatives, antioxidants, spreading agents, colorants and thickeners, and
   (e) water.

2. A method for controlling animal pests, comprising applying a composition according to claim 1 to animal pests and/or their habitat.

3. A method for controlling phytopathogenic fungi comprising applying a composition according to claim 1 to plants, plant parts, plant seeds and/or an area on which plants grow.

4. A method for controlling unwanted vegetation comprising applying an effective amount of a composition of claim 1 to unwanted vegetation and/or their habitat.

5. The composition of claim 1, wherein said penetrant comprise ethoxylate rapeseed oil with a degree of ethoxylation from 60% by weight to 80% by weight.

6. The composition of claim 1, wherein said composition comprises from 1 to 20% by weight of at least one nonionic surfactant.

7. The composition of claim 1, wherein said composition comprises from 1 to 20% by weight of at least one anionic surfactant.

* * * * *